(12) United States Patent
Weber et al.

(10) Patent No.: US 7,493,182 B2
(45) Date of Patent: Feb. 17, 2009

(54) METHOD AND DEVICE WITH REGARD TO DATA TRANSMISSION IN THE PRODUCTION OF DENTURE PARTS

(75) Inventors: Gerhard Weber, Inning/Ammersee (DE); Stephan Holzner, Mühldorf/Inn (DE)

(73) Assignee: Aepsilon, GmbH, Graefelfing (DE)

( * ) Notice: Subject to any disclaimer, the term of this patent is extended or adjusted under 35 U.S.C. 154(b) by 0 days.

(21) Appl. No.: 11/400,043

(22) Filed: Apr. 7, 2006

(65) Prior Publication Data

US 2006/0253212 A1 Nov. 9, 2006

(30) Foreign Application Priority Data

Apr. 8, 2005 (DE) ........................ 10 2005 016 233

(51) Int. Cl.
  *A61C 5/10* (2006.01)
  *G06F 19/00* (2006.01)
(52) U.S. Cl. .................... 700/95; 700/117; 433/223
(58) Field of Classification Search .................. 700/95, 700/117; 433/223
  See application file for complete search history.

(56) References Cited

U.S. PATENT DOCUMENTS

| | | | | |
|---|---|---|---|---|
| 5,690,490 A * | 11/1997 | Cannon et al. ............... 433/141 |
| 6,567,770 B2 * | 5/2003 | Dorough ..................... 702/188 |
| 6,575,751 B1 * | 6/2003 | Lehmann et al. ............. 433/223 |
| 6,600,168 B1 * | 7/2003 | Geng ..................... 250/559.22 |
| 6,835,066 B2 | 12/2004 | Iiyama et al. |
| 6,847,334 B2 * | 1/2005 | Hayhurst et al. .............. 345/1.2 |
| 6,882,894 B2 * | 4/2005 | Durbin et al. ................ 700/118 |
| 6,968,247 B2 | 11/2005 | Rathke et al. |
| 2005/0003329 A1 | 1/2005 | Lehmann et al. |

FOREIGN PATENT DOCUMENTS

| | | |
|---|---|---|
| DE | 9421146 U1 | 8/1995 |
| DE | 19828003 A1 | 1/2000 |
| DE | 10203665 A1 | 11/2002 |
| DE | 10301643 A1 | 8/2004 |

* cited by examiner

*Primary Examiner*—Michael D Masinick
(74) *Attorney, Agent, or Firm*—IP Strategies

(57) ABSTRACT

The invention relates to a method in which at a first location (A), such as a dental technician's laboratory or a dentist's surgery, digital image data (18) in the form of single images and/or image sequences are generated and these are transmitted to a second location (B), such as a production centre for denture parts, wherein the digital image data (18) and/or image sequences relate to information on the manufacture of denture parts (15). Furthermore, the invention relates to a scanning device for obtaining data records of dental models with a scanning appliance, such as a scanning head and with a camera, wherein remote data transmission means (8) are provided for transmitting digital image data (18) from the camera in the form of single images and/or image sequences to another location (B), such as a production centre.

19 Claims, 5 Drawing Sheets

Figure 1A:
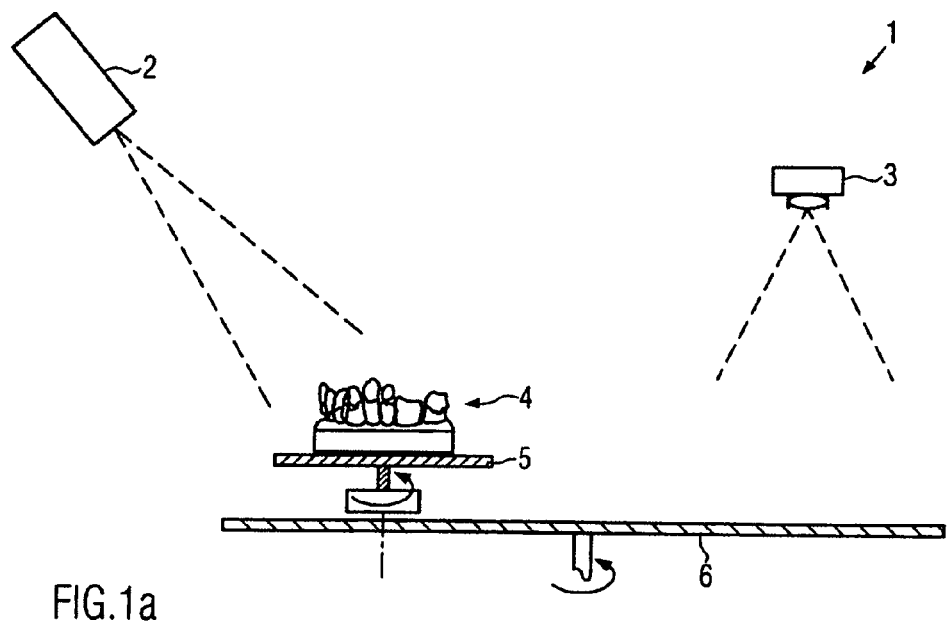

METHOD AND DEVICE WITH REGARD TO DATA TRANSMISSION IN THE PRODUCTION OF DENTURE PARTS

In the automatic production of denture parts, such as bridges, inlays, overlays or similar items, the automatic acquisition of the shape of a residual dental region based on a plaster model, the simulation of a denture part based on this data record and the transmission of the data describing the denture part via the Internet to a production centre are known. In the production centre the denture part is produced based on the transmitted data and then dispatched. The generation of the data records for the denture part can for example occur in a dental technician's laboratory or at a dentist's surgery.

Occasionally it occurs that the denture part does not fit or does not fit well on the model of the residual dental region or on the residual dental region itself. This leads to the situation in which the denture part must be reworked or even produced again. The cause of the error can however often not be unambiguously found due to the various steps in the method.

The object of the invention is therefore to improve the automated production of denture parts.

With the method, at a first location, at which for example the model of the residual dental region or the patient himself is located, digital image data are produced.

These digital image data may be single pictures or picture sequences (films).

These digital image data are remotely transmitted to a second location. This location may be for example the production centre for denture parts or an associated call centre (which may also be situated at a location other than that of the production centre) or similar facility. The second location can also be that of a company which has supplied a system, a scanning device and/or a denture part manufacturing machine, such as a milling machine.

The transmitted data relate to image data and/or image sequences containing information regarding the manufacture of denture parts. These image data may for example be the image data of the denture parts, the dental models such as plaster models, the residual dental region or advantageously combinations of these. It is particularly advantageous to produce for example image data which show the dental model together with the denture part. Also image sequences, which show how a denture part can be mounted on a dental model or similar item or how such a mounting does not function, can be produced and transmitted. The transmission occurs preferably via the Internet or telephone lines, DSL connections, mobile radio or similar system or combinations of the various telecommunication equipment. The image data can be transmitted in real time similar to a type of television transmission, but can also be time shifted or time delayed also until after possible saving at the first location.

The image data are normally obtained with a camera, wherein the camera preferably is part of a scanning device for dental models. Theses types of scanning device are generally equipped without a camera, but can also comprise a camera (refer to DE 10 2004 051165). Here the camera is provided to localise certain areas of a dental model without however transmitting image data in any manner.

With this method it is also possible from the production centre or the second location to assess whether the denture part fits well or badly on the dental model or on the residual dental region, respectively or errors in the production chain can be identified. Also, systematic errors in the manufacture of the denture parts can be detected and corrected. These may for example be errors which always occur with certain rare forms of denture parts which otherwise cannot be detected.

With this method it is therefore possible on one hand to examine the individually produced denture part in connection with the plaster model from a production centre; on the other hand it facilitates the identification of recurring errors and the localisation of possible error sources.

The camera is either permanently connected to a scanning device or to a computer connected to the scanning device or capable of communication with the scanning device via a cable or via a wireless communications link to the scanning device or to the computer.

In a preferred embodiment the image data are displayed at the second location. Consequently it is possible for an operating person at the second location to assess for example the denture part in combination with a dental model.

Advantageously also audio signals are transmitted between the first and second locations or in the reverse direction. This enables an operating person in the production centre to communicate by speech with another person for example in the dental technician's laboratory or in a dentist's surgery and to discuss the case.

Furthermore, an embodiment of the method is advantageous in which the transmitted image and audio data are saved at the second location for purposes of documentation. This facilitates the utilisation of these data for quality assurance and similar activities.

One embodiment is particularly advantageous in which a third further location can be switched in to transmit audio and/or video signals to there or from there. This may facilitate for example the inclusion of the dentist in the discussion of a case.

Also advantageous is an automated image evaluation at the first or second location. Thus, it is possible for example to automatically determine the sizes of gaps between the denture part and the tooth stump or similar feature and thus to determine an objective measure for an incorrect shape of the denture part.

Also, with a denture part which is too loosely seated, it can be brought into an abutment position moving it in one direction, then an image can be recorded and the denture part brought into another abutment position by moving it in another direction, an image can be recorded again and both images compared. Thus, a measure for the loosely seated denture part or for the wobbling of the denture part can be obtained with automatic image evaluation.

With the method it is also possible to transmit image data already before the manufacture of the denture part from the first to the second location. This may be relevant for example to discuss questions relating to the basic manufacturing feasibility of a denture part in a production centre.

It is also possible in this way to monitor from the second location the generation of data records which represent the shape of a model or to provide help or instructions. The help or instructions can either be realised by an operating person or automatically by appropriate software at the second location.

It is also possible to give instructions, help, directions or similar information of any type from the second location to the first location over the audio link. It is also possible to give control commands from the second location to a scanning device at the first location, for example to implement single and/or all automated steps during the scanning of a model.

A scanning device comprises a mechanical or optical scanning appliance, such as a scanning head with which the surface of dental models can be scanned to thus obtain digital data records which describe the dental model.

Furthermore, the scanning device comprises a camera.

Furthermore, means of transmission is provided with which digital image data, which has been obtained with the camera, can be transmitted to another remotely situated location, such as for example a production centre. For better communication with the production centre, the scanning device or a computer connected to it is furthermore advantageously equipped with a microphone and/or a loudspeaker with which the audio data can be recorded or output. The camera on the scanning device can be permanently joined to the scanning device or also removable, wherein it is then connected to the scanning device with a cable or through wireless means for the data transmission.

Figure 2:
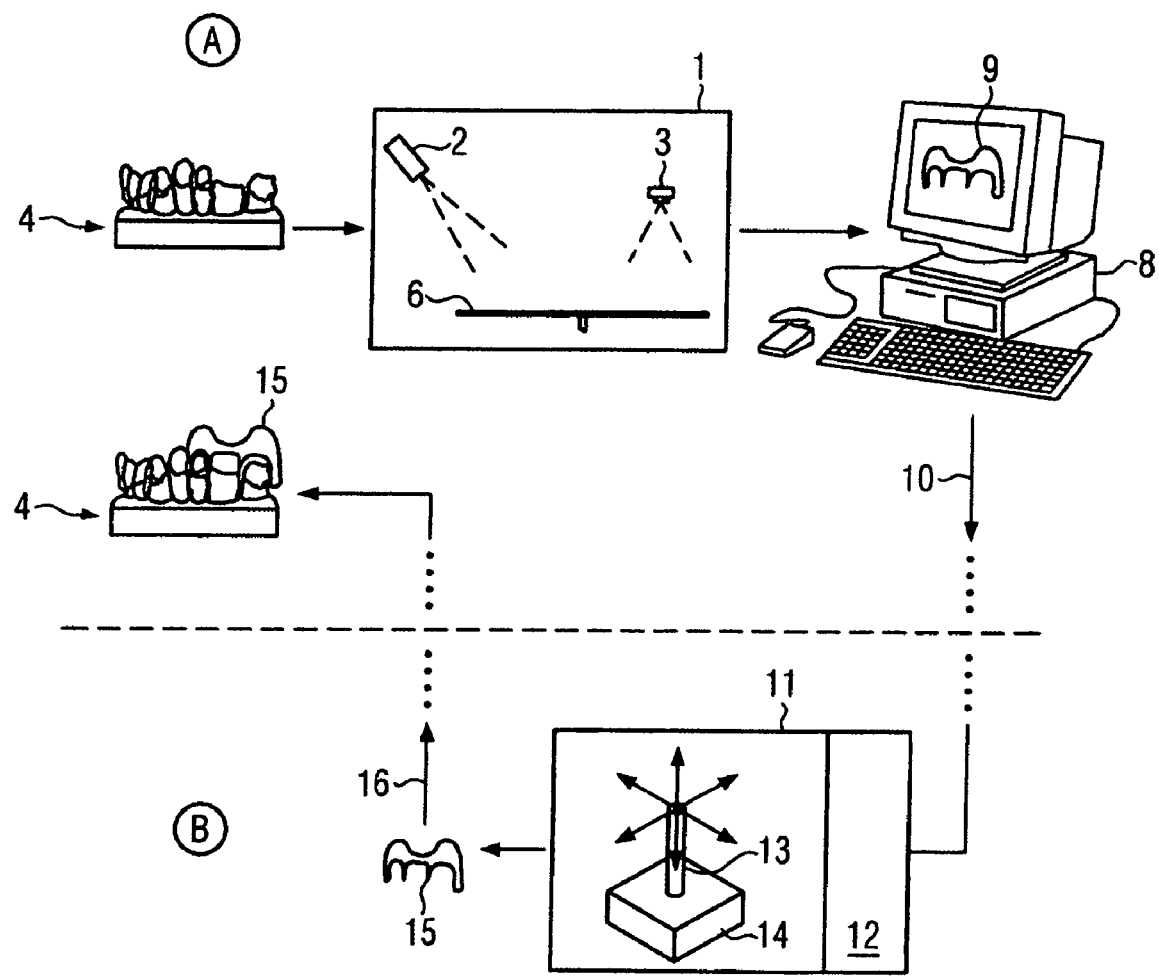
Figure 3:
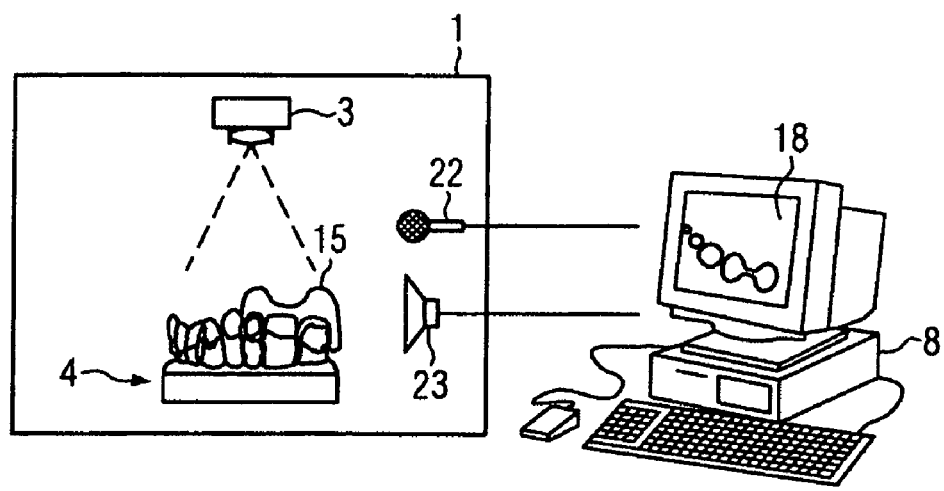
Figure 3:
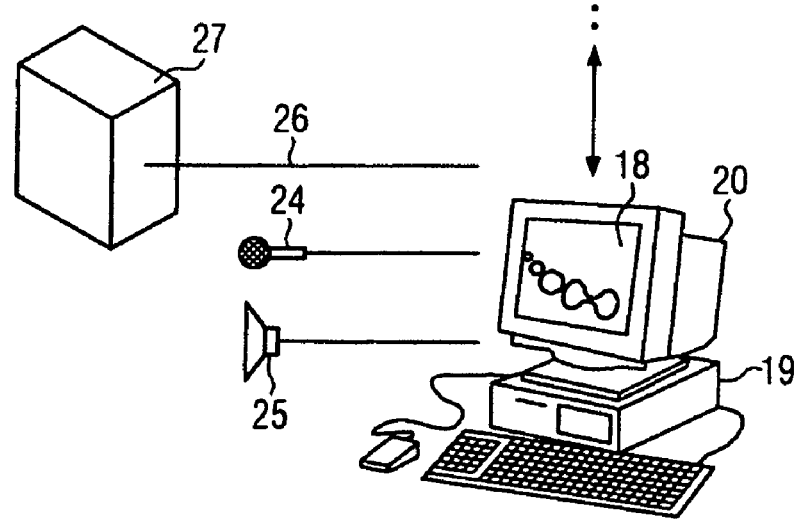
Figure 4A:
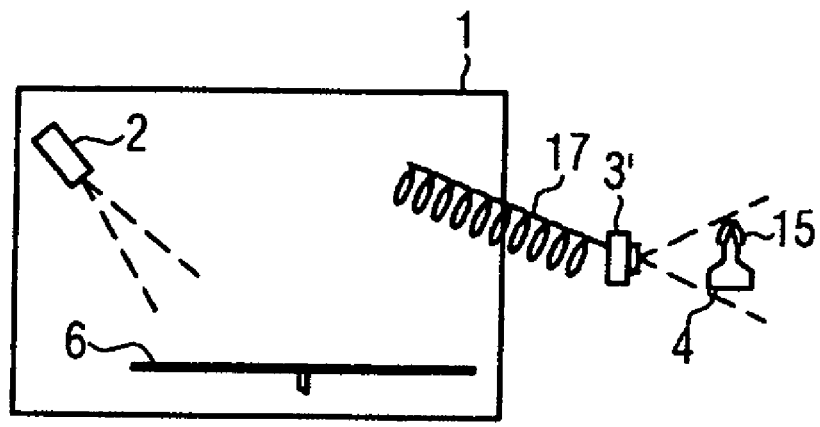
Figure 4B:
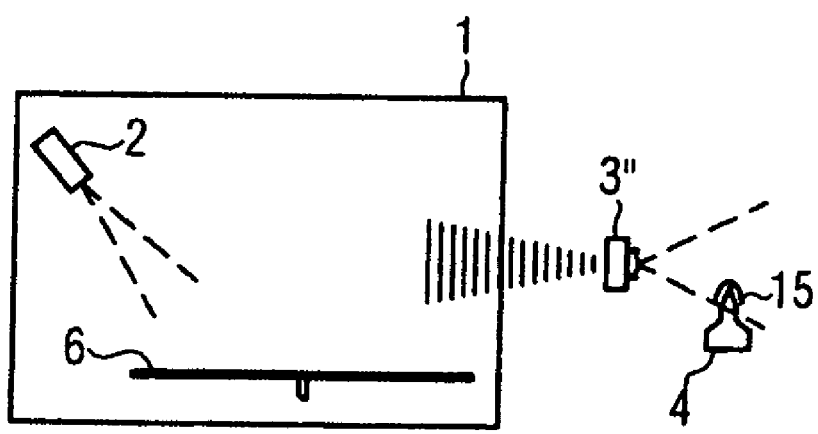
Figure 5:
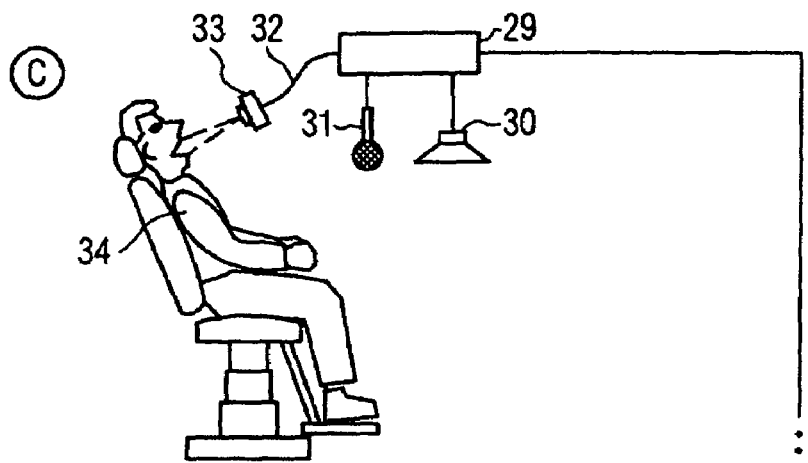
Figure 5:
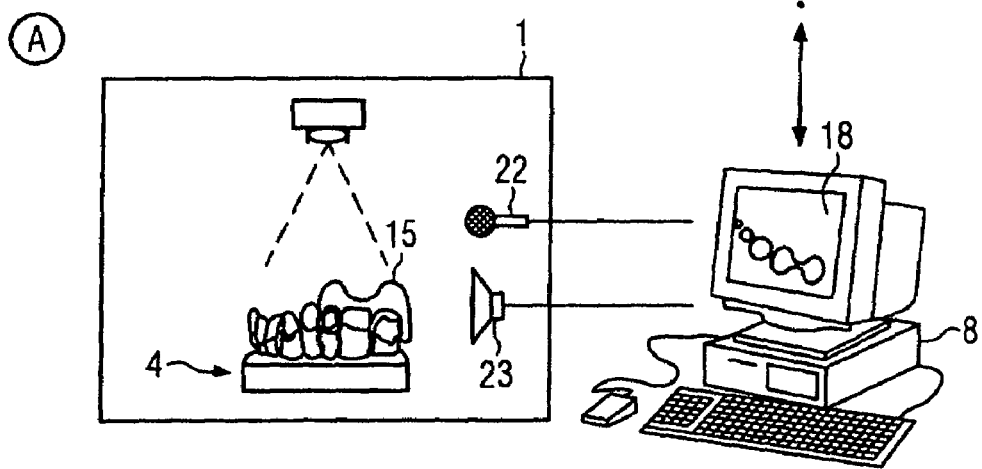
Figure 5:
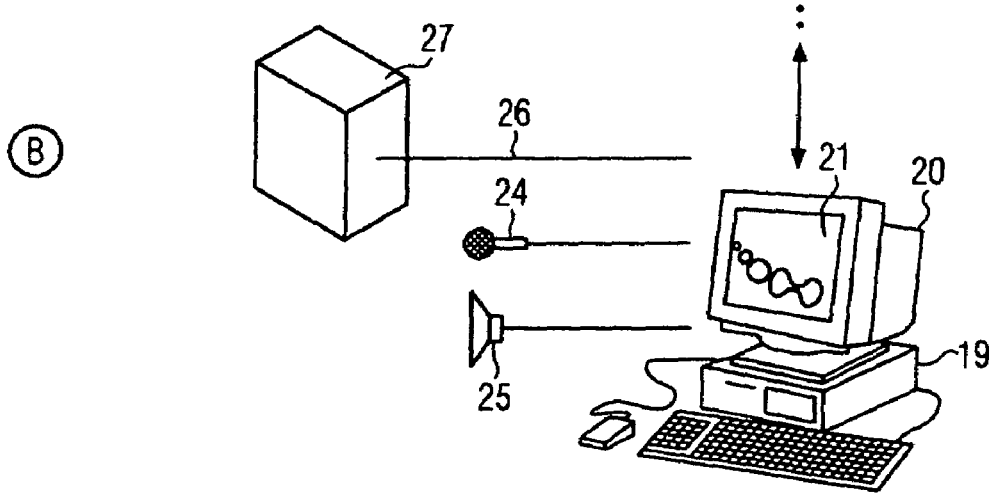

Advantageous embodiments are explained based on the enclosed figures. The following are illustrated:

FIG. 1 a schematic illustration of a scanning device,

FIG. 2 a schematic illustration of the devices at the first and second locations, FIG. 3 a schematic illustration of the devices at the first and second locations, FIG. 4 a schematic illustration of a scanning device and a camera, FIG. 5 a schematic illustration of the devices at the first, second and third locations.

Figure 1B:
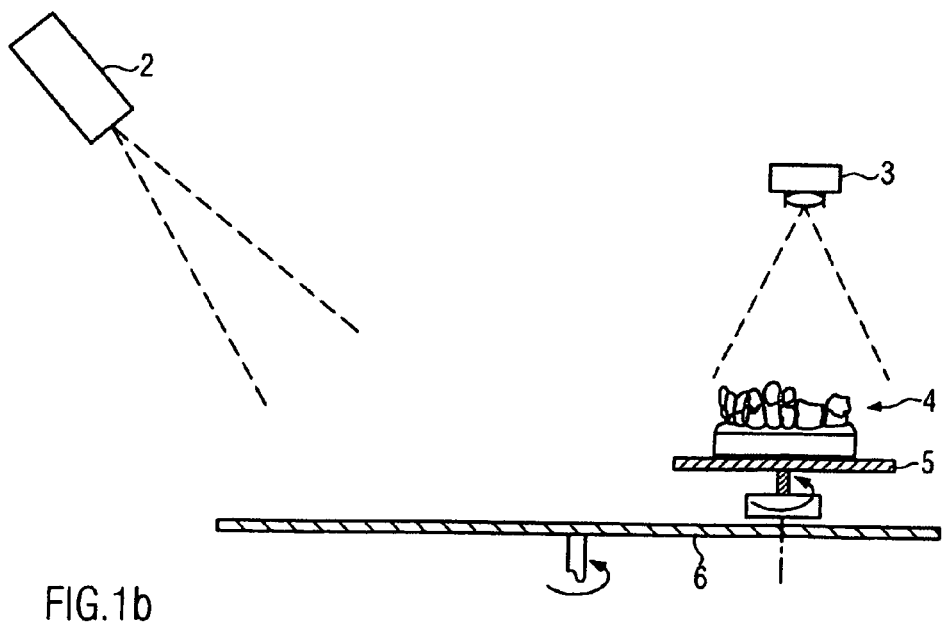

In FIG. 1 a scanning device 1 with a scanning appliance 2 is illustrated. The scanning appliance 2 can be an optical or mechanical scanning head with which it is possible to scan the surface or parts of the surface of a model 4 of a residual dental region and thus to digitise it. The model 4, which for example may be a plaster model, is in this respect for example supported on a rotating plate 5, which in turn is supported on a rotating plate 6. The model 4 can be brought under a camera 3 with the rotating plate 6 (refer to FIG. 1b). An image of the model 4 can be recorded with the camera 3 to fix regions within which scanning of the model 4 occurs with the scanning head 2. The camera 3 is generally used for the optimum acquisition of the shape of the model 4.

The camera 3 can be plugged into or onto the scanning device in a defined position. It can be permanently connected or also removable.

In FIG. 2 the automated operation during the manufacture of denture parts is illustrated in an overview. A model 4 is brought into a scanning device 1 (also called a scanner) where it is scanned with the aid of the camera 3 and a scanning head 2. The acquired data are saved in a computer 8, so that the data record 9 of a denture part can be modelled with the computer 8. This data record 9 is transmitted with suitable remote data transmission means 10 to a second location (B). At the location (B), which can be the production centre, the data of the denture part 9 are received with a suitable device 12, evaluated and appropriately conditioned for production with a machine. A milling machine 13 schematically illustrated in FIG. 2 mills a denture part 15 from a blank 14. This is packaged at the location (B) and dispatched to the location (A). At the location (A) the denture part 15, which has been made by the machine, is mounted on the dental model 4.

As illustrated in FIG. 3, the model 4 or the denture part 15 or both can be inserted into the device 1, so that the camera 3 can record one or more images of the model 4, the denture part 15 or both in combination. In this respect the model 4 and/or the denture part 15 can be supported on the rotating table 6 or the rotating table 5, but can also be arranged in any other position relative to the camera 3, for example also in that it is brought into an appropriate position manually. The device 1 in FIG. 3 can be the same as in FIG. 1 or 2, but can also be a separate device which is independent in this regard.

The camera 3 can also record image sequences, i.e. films or similar sequences. This method is particularly practicable when the denture part 15 does not fit or does not fit well or does not fit well enough on the plaster model 4 or the dental technician is of the opinion that the denture part 15 does not fit or does not fit well or does not fit well enough. A film can illustrate, for example, how attempts at mounting the denture part 15 on the model 4 fail.

The image data 18 recorded by the camera are transmitted from the location (A) to the location (B), i.e. for example, the production centre. In this way at the location of the production centre a visual impression of the denture part 15 can be obtained in combination with the model 4 in order to be able to assess whether the denture part 15 is inadequate or whether the denture part 15 is in order.

If the location (B) is the location of the manufacturer of the scanning device and/or of the denture-part manufacturing device, this machine manufacturer can obtain an impression of how his machines function individually or as a complete system. The scanning device 1 or the computer 8 connected to it at location (A) can furthermore comprise a microphone 22 and a loudspeaker 23 and a microphone 24 and a loudspeaker 25 can be provided at the location (B). The microphone 22 and loudspeaker 23 are formed such that both with an open as well as a closed scanning device 1 an audio communication is possible by an operating person adjacent the scanning device 1. Audio data can be transmitted to and fro between the scanning device 1, respectively the connected computer 8, and an appropriate device 19 at the location (B). Consequently it is possible for a dental technician or a dentist at the location (A) to comment on the image data with an operating person at the location (B). Also instructions on orientating the model 4 or the denture part 15 or both can be given by the operating person at the location (B), so that a good impression of the denture part/model can be obtained with the camera 3 at the location (B). The instructions can be transmitted through the audio link to an operating person at the location (B) as well as in the form of control signals to the scanning device 1. Here, for example, the rotating tables 5 and/or 6 and/or the camera 3 can be remotely controlled. The relative position between the model 4 and the camera 3, the optical or electronic magnification, focus, brightness or similar parameters can be adjusted.

The image or audio data transmitted to the location (B) can be saved with an appropriate storage device 27 through an appropriate data transmission 26 for documentation purposes. It is also possible to pass the transmitted data for later quality assurance or to the development department in order to detect and eliminate systematic errors in the manufacturing process, as illustrated in FIG. 2. Also, images, which are saved for documentation purposes, can be made before the dispatch of the denture parts at the location (B). These saved data can then be recalled in the method.

In order to assess how a denture part 15 is seated on a model 4, the denture part 15 must first be manufactured. The implementation of the method is however already practicable before the manufacture of the denture part. For example, the production centre can be consulted before the manufacture of the denture part to ascertain whether a certain denture part 15 can be basically manufactured or how it is best manufactured or with which material, etc.

With the camera 3 the scanning of the model 4 at the location (A) can however also be monitored by a person or software at the location (B). The person or the software at the location (B) can then transmit instructions on the operation of the scanning device or control commands to the scanning device. These instructions or control commands refer for example to the production of the data record of the model, i.e. scanning of the model. In this way training of a person at the location (A) or support for problems with scanning at the location (A) can be provided. Also instructions on the operation of the software used for generating the data record of the denture part can thus be given. Also, training on the use of the software for scanning or for modelling the denture part can take place.

In FIG. 4a it is shown that the camera 3 can also be removed from the scanning device 1 in order to be able to bring it into a suitable position relative to the model 4 with the denture part 15. The model 4 does not always need to be placed again into the scanning device. The camera 3' here is still connected by a cable 17 to the device 1, so that the image data recorded by the camera 3' can be transmitted to the scanning device 1 (refer to FIG. 4a).

FIG. 4b furthermore schematically shows that instead of a cable 17 also an appropriate data transmission can occur by radio, infrared or similar method.

It is also possible that the camera 3 in a state removed from the scanning device 1 initially saves recorded image data and these data are then transmitted to the scanning device 1 or to the connected computer 8 when the camera 3 is again inserted into the scanning device 1.

The camera 3 can also be connected to the computer 8 instead of to the device 1 in order to transmit image data directly to the computer, either by cable, radio, infrared or the above mentioned memory technology.

FIG. 5 shows how, in addition to the data transmission between the locations (A) and (B), a third location (C) can be switched in. This may be, for example, the dentist with whom a patient 34 is located. Here an appliance 29 is provided which comprises a camera 33 which can communicate to the appliance 29 via a cable 32 or appropriate radio or memory technology described above. With the camera 33 images of the oral cavity or the residual dental region of the patient 34 can be recorded and transmitted to the location (A) and/or (B). For simpler communication the device 29 can also comprise a microphone 31 and a loudspeaker 30 so that audio communication with the location (A) and/or (B) is also possible.

Instead of or in addition to the dentist, a company, which supplies and/or has supplied the materials for the denture part, can also be switched in (for video and/or audio transmission).

The invention claimed is:

1. Method, comprising:
    providing a scanning device that comprises a scanning appliance and a camera,
    scanning a shape of a dental model using the scanning appliance, at a first location,
    modeling a data record for a denture part, at the first location,
    transmitting the data record of the denture part from the first location to a second location, and
    manufacturing the denture part at the second location by automated means,
    dispatching the denture part from the second location to the first location,
    generating, using the camera at the first location, digital image data in the form of at least one of single images and image sequences,
    transmitting the digital image data to the second location,
    wherein the at least one of digital image data and image sequences relate to information on the manufacture of denture parts and show the denture part, and
    assessing at the second location via image data from the first location whether the denture part fits well or badly on the dental model.

2. Method according to claim 1, wherein the digital image data comprise images of the dental model.

3. Method according to claim 1, wherein transmitting the digital image data takes place via one of the Internet, a telephone line, DSL, and mobile radio.

4. Method according to claim 1, further comprising linking the camera to a computer connected to the scanning device.

5. Method according to claim 1, wherein the camera is permanently connected to the scanning device.

6. Method according to claim 1, further comprising displaying the transmitted digital image data at the second location on at least one of a monitor and a hardcopy printout.

7. Method according to claim 1, further comprising transmitting audio signals between the first location and the second location.

8. Method according to claim 7, further comprising saving at least one of the digital image data and the audio signals at the second location.

9. Method according to claim 7, further comprising transmitting at least one of the digital image data and the audio signals to a third location, to enable a tripartite conference connection among the third location, the first location, and the second location.

10. Method according to claim 9, wherein the third location is defined by a location of one of a dentist and dental technician.

11. Method according to claim 1, further comprising
    making a decision about a new manufacture of denture parts, and
    recording the decision in a production planning department at the second location,
    wherein the decision is made at the second location at least one of automatically and according to data entry by an operating person.

12. Method according to claim 1, further comprising automatically evaluating the digital image data at one of the first location and the second location.

13. Method according to claim 1, further comprising transmitting at least one of instructions for operation of the scanning device and control commands from the second location to the scanning device, wherein the at least one of instructions and control commands relate to generation of a data record of a dental model.

14. Method according to claim 1, wherein the first location is one of a dental technician's laboratory and a dentist's surgery.

15. Method according to claim 1, wherein the second location is a production centre for denture parts.

16. Method according to claim 1, wherein the at least one of digital image data and image sequences includes digital image data that show one of a dental model together with the denture part and a residual dental region together with the denture part.

17. Method according to claim 2, wherein the dental model is a plaster model.

18. Method according to claim 1, wherein the camera is removably coupled to the scanning appliance and is adapted to communicate with at least one of the scanning device and a computer via one of a cable and wireless means, wherein the wireless means includes one of radio frequency communication and an infrared interface.

19. Method according to claim 1, further comprising
    assessing that the denture part is too loosely seated on the dental model,
    bringing the denture part into a first abutment position by moving the denture part in a first direction,
    recording a first image of the denture part in the first abutment position,
    bringing the denture part into a second abutment position by moving the denture part in a second direction,
    recording a second image of the denture part in the second abutment position, and
    comparing the first image and the second image.

* * * * *